US010830770B2

(12) United States Patent
Maring et al.

(10) Patent No.: US 10,830,770 B2
(45) Date of Patent: *Nov. 10, 2020

(54) CELL DEATH ASSAY (71) Applicant: HQ MEDICAL (NETHERLANDS) B.V., Rotterdam (NL)

(72) Inventors: Markwin Hendrik Maring, Rotterdam (NL); Clemens Waltherus Gerardus Löwik, Rotterdam (NL); Ermond Reijer Van Beek, Rotterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/377,059

(22) PCT Filed: Feb. 6, 2013

(86) PCT No.: PCT/NL2013/050064
§ 371 (c)(1),
(2) Date: Aug. 6, 2014

(87) PCT Pub. No.: WO2013/119111
PCT Pub. Date: Aug. 15, 2013

(65) Prior Publication Data
US 2015/0010921 A1 Jan. 8, 2015

(30) Foreign Application Priority Data

Feb. 6, 2012 (NL) .................................... 2008241

(51) Int. Cl.
| | | |
|---|---|---|
| *G01N 33/569* | (2006.01) | |
| *G01N 33/533* | (2006.01) | |
| *G01N 33/50* | (2006.01) | |
| *A61K 31/352* | (2006.01) | |
| *A61K 31/403* | (2006.01) | |
| *A61K 31/404* | (2006.01) | |
| *C07K 14/435* | (2006.01) | |
| *G01N 33/574* | (2006.01) | |
| *G01N 33/58* | (2006.01) | |
| *C07D 209/24* | (2006.01) | |
| *C07D 498/14* | (2006.01) | |
| *C07D 498/22* | (2006.01) | |

(52) U.S. Cl.
CPC ..... *G01N 33/56966* (2013.01); *A61K 31/352* (2013.01); *A61K 31/403* (2013.01); *A61K 31/404* (2013.01); *C07D 209/24* (2013.01); *C07D 498/14* (2013.01); *C07D 498/22* (2013.01); *C07K 14/435* (2013.01); *G01N 33/5008* (2013.01); *G01N 33/5091* (2013.01); *G01N 33/533* (2013.01); *G01N 33/57496* (2013.01); *G01N 33/583* (2013.01); *G01N 2500/10* (2013.01); *G01N 2510/00* (2013.01); *G01N 2800/52* (2013.01)

(58) Field of Classification Search
CPC ......... G01N 33/5008; G01N 33/56966; G01N 33/533
See application file for complete search history.

(56) References Cited

U.S. PATENT DOCUMENTS

| | | | | |
|---|---|---|---|---|
| 6,291,203 B1* | 9/2001 | Poot | ........................ | C09B 23/02 435/40.5 |
| 6,974,873 B2* | 12/2005 | Leung | ................ | A61K 41/0057 548/455 |
| 2008/0038773 A1* | 2/2008 | Filanoski | ................. | G01N 1/30 435/40.5 |
| 2010/0284922 A1* | 11/2010 | Cordeiro | ............ | A61K 49/0004 424/9.1 |
| 2015/0004626 A1* | 1/2015 | Maring | .............. | G01N 33/5008 435/7.4 |
| 2016/0106851 A1* | 4/2016 | Maring | .............. | A61K 49/0032 424/9.6 |

OTHER PUBLICATIONS

Vyakarnam et al., "A Comparative Nuclear Localization Study of Galectin-1 with Other Splicing Components," Experimental Cell Research, vol. 242, pp. 419-428, published 1998.*
Levelt et al., "Streptavidin-Tricolor is a Reliable Marker for Nonviable Cells Subjected to Permeabilization or Fixation," Cytometry, vol. 15, pp. 84-86, 1994.*
Ernst et al., "Cyanine Dye Labeling Reagents for Sulfhydryl Groups," Cytometry, vol. 10, pp. 3-10, published Jan. 1989.*
Liljas et al., "Textbook of Structural Biology", World Scientific Publishing Company, published 2009.*
Perfetto et al., "Amine reactive dyes: An effective tool to discriminate live and dead cells in polychromatic flow cytometry", Journal of Immunological Methods, vol. 313, pp. 199-208, published 2006.*
Heilemann et al., "Subdiffraction-Resolution Fluorescence Imaging with Conventional Fluorescent Probes", Angew. Chem. Int. Ed., vol. 47, pp. 6172-6176, published Jul. 22, 2008.*
Tung et al., "Traceless and Chemoselective Amine Bioconjugation via Phthalimidine Formation in Native Protein Modification", Org. Lett., vol. 18, pp. 2600-2603, published May 18, 2016.*
Inui et al., "Annexin VI Binds to a Synaptic Vesicle Protein, Synapsin I", J. Neurochem. vol. 63, No. 5, pp. 1917-1923, published 1994.*
Scitable by Nature Education (print retrieved on Sep. 25, 2018, https://www.nature.com/scitable/definition/cytoplasm-280) (Year: 2018).*
International Preliminary Report on Patentability dated Aug. 12, 2014 issued in connection with PCT/NL2013/050064.

(Continued)

Primary Examiner — Tracy Vivlemore
Assistant Examiner — Nam P Nguyen
(74) Attorney, Agent, or Firm — Akerman LLP (57) ABSTRACT The present invention relates to a method for detecting cell death using a luminescent compound; to the luminescent compounds for particular uses; to a kit comprising said compounds and to a protein. The method is applicable for detecting cell death, essentially regardless of the mechanism through which cell death occurred or is occurring and is therefore not limited e.g. to detecting cell death resulting from only one mechanism selected from apoptosis and necrosis.

9 Claims, 5 Drawing Sheets (56) References Cited

OTHER PUBLICATIONS

Written Opinion of the International Searching Authority dated Jun. 13, 2013 issued in connection with PCT/NL2013/050064.
International Search Report dated Jun. 13, 2013 issued in connection with PCT/NL2013/050064.
Hashimoto et al., "Atypical X-linked Agammaglobulinemia Diagnosed in Three Adults", Internal Medicine, Tokyo, Japan, vol. 38, No. 9, Sep. 1999, pp. 722-725.
Mastroianni et al., "Alteration of Laminin Production in Small-Cell Lung Carcinoma: Possible Correlation with the Absence of the Basement Membrane", Tumour Biology: The Journal of the International Society for Oncodevelopmental Biology and Medicine, 1993, vol. 14, No. 5, pp. 279-287.

* cited by examiner

II, III

II, III

CELL DEATH ASSAY

This application is a national phase of PCT/NL2013/050064, filed Feb. 6, 2013, and claims priority to NL 2008241, filed Feb. 6, 2012, the entire contents of both of which are hereby incorporated by reference.

FIELD OF THE INVENTION

The present invention is in the field of a cell death probe, a method for detecting cell death, compounds for detecting cell death, and an assay kit.

BACKGROUND OF THE INVENTION

Excessive cell death is characteristic of vascular disorders, neurodegenerative diseases, myelodysplastic syndromes, ischemia/reperfusion injury and organ transplant rejection, among others. Cell death also plays a role in the treatment of disease. In cancer, for example, most chemotherapeutics, radiation treatments and anti-hormonal agents act by inducing death of cancer cells.

Cell death plays an important role in development and normal tissue- or cell turnover like e.g. skin, gut, hair, and in the reproductive and immune system. Under normal physiological conditions cell death is strictly regulated and an imbalance is usually associated with diseases, like e.g. ischemia-reperfusion injury as can occur after stroke or myocardial infarction, neurodegenerative diseases, myelodysplatic diseases, rejection after transplantation of organs or cells, vascular diseases and psoriasis. Cell death, predominantly necrosis, can also occur after trauma or complete (local) lack of oxygen. Cell death also plays a role in the treatment of disease. In cancer, for example, most chemotherapeutics, radiation treatments and anti-hormonal agents act by inducing death of cancer cells.

Since cell death plays such an important role in many diseases, non-invasive imaging of this process is highly desirable and needed i.e., as a diagnostic tool for early detection and progression of diseases and to follow therapeutic effects of therapies. This will allow not only to determine the degree of tissue injury after e.g. myocardial infarction or stroke and to identify vulnerable plaques in atherosclerosis but also i.e. to monitor treatment response in cancer.

Methods for detecting cell death are known in the prior art.

Labeled Annexin V is widely used as a cell death (specifically apoptosis) imaging agent. Annexin V is an endogenous human protein which binds to Phosphotidyl Serine (PS) with very high affinity. During apoptosis PS is believed to be externalized by a flip-flop mechanism in the outer plasma membrane making them recognizable for macrophages that will engulf and remove the apoptotic cells.

Annexin V has been extensively used in in vitro cell assays using fluorescent labels. Annexin V has also been evaluated in clinical trials for various applications like e.g. monitoring cell death in stroke, myocardial infarction, rheumatoid arthritis, Alzheimer's disease and tumors after chemo or radio-therapy. In most studies Annexin was radiolabeled with 99$^m$Tc (Technetium). The labeling process that was used in the early studies is cumbersome with very low labeling efficiency. Apart from that, the technetium labeled Annexin-V showed a high degree of non-specific uptake in the kidneys, liver and bladder (urine), and also biliary excretion into the bowel making imaging of the abdominal region impossible.

The main problems with technetium-labeled Annexin-V are its large size, resulting in slow delivery to site of interest, non specific uptake in non target tissues, and poor biodistribution. Furthermore, low clearance of the radio-labeled probe will result in prolonged residency of the tracer in the body resulting in high effective doses of radiation for the patient. Apart from these problems there is also concern about the specificity of Annexin V for dying cells. This is because PS is also externalized in endothelial cells, macrophages, activated platelets and erythrocytes. PS externalization does not necessarily represent cells committed to the cell death pathway. It is known that PS can also be reversibly externalized independent of apoptosis, especially in situations of physiological stress. In ischemic reperfusion injury relatively high Annexin V uptake is most probably due to a large number of stressed cells and not to only a few real apoptotic cells with high PS expression that are committed to die.

Other techniques that are commonly applied for identifying apoptosis in in vitro assays include: monitoring caspase activity; monitoring molecules in the mitochondria that are indicators of apoptosis such as cytochrome c; identifying loss of membrane phospholipid symmetry, and; identifying DNA fragmentation. A detailed discussion of these techniques and their disadvantages is to be found in "*Apoptosis: A Review of Programmed Cell Death*", S. Elmore, *Toxicologic Pathology*, 2007, 35, 495-516.

Few of the methods of the prior art that can detect cell death are suitable for detecting cell death per se; as is the case for the above examples, they are specific for detecting apoptosis, usually through detecting some transient state or intermediate compound resulting from a cell undergoing apoptosis. It is important to make a distinction between apoptosis and cell death per se. Apoptosis relates to programmed cell death, which involves the genetically determined elimination of cells; detecting cell death per se is mechanism independent and relates to detecting cells that are dead as a result of any cell death mechanism.

It is also noted that apoptosis is also only one form of programmed cell death, other forms of programmed cell death have been described and other forms of programmed cell death may yet be discovered. An alternative to apoptotic cell death is necrosis: a process whereby the cell follows an energy-independent mode of death. Although the mechanisms and morphologies of apoptosis and necrosis differ, there is overlap between these two processes and cell death may also occur as a result of other mechanisms that cannot be defined either as purely apoptosis or necrosis.

One example of a more general method to detect cell death, and one that is commonly used in live/dead assays, is to apply a dye to a population of cells wherein the dye becomes fluorescent upon intercalating into DNA; the best-known example of such a dye is propidium iodide (PI). In healthy cells the dye and cellular DNA are kept separate by the cell membrane, the nuclear membrane and the mitochondrial membranes; only upon cell death do these membranes become permeable such that DNA and the dye can come into contact. The fluorescence intensity is proportional to the number of dead cells in the population. Such compounds are typically very toxic and hence cannot be used except for in in vitro assays.

Some prior art documents specifically relate to apoptosis and detection thereof. Steegmaier et al., in "BI 2536, a potent and selective inhibitor of polo-like kinase 1, inhibits tumor growth in vivo", Current Biology, Current Science, GB, part 17, nr. 4, Feb. 20, 2007, p. 316-322, and Petrovsky et al., in "Near-infrared fluorescent imaging of tumor apoptosis", Cancer Research 15 Apr. 2003, LNKD-PUBMED: 12702586, vol. 63, nr. 8. Apr. 15, 2003, p. 1936-1942, use cyanine labeled Annexin V for detecting apoptosis. Schellenberger EYK et al., in "Optical imaging of apoptosis as a biomarker of tumor response to chemotherapy", Neoplasia (New York, N.Y.) 2003 May-June, LNKD-PUBMED: 12869301, Vol. 5, nr. 3, May 2003, p. 187-192, describe optical imaging of apoptosis as a biomarker of tumor response to chemotherapy. The above mentioned disadvantage applies largely.

The present invention therefore relates to a method, compounds and a kit for detecting cell death, which overcomes one or more of the above disadvantages.

SUMMARY OF THE INVENTION

The present invention relates to a method for detecting cell death using e.g. a luminescent compound, said compound being a cyanine or rhodamine; to the luminescent compounds for particular uses; and to a kit comprising said compounds. The method is applicable for detecting cell death, essentially regardless of the mechanism through which cell death occurred or is occurring and is therefore not limited e.g. to detecting cell death resulting from only one mechanism selected from apoptosis and necrosis.

Figures 1, 1A:
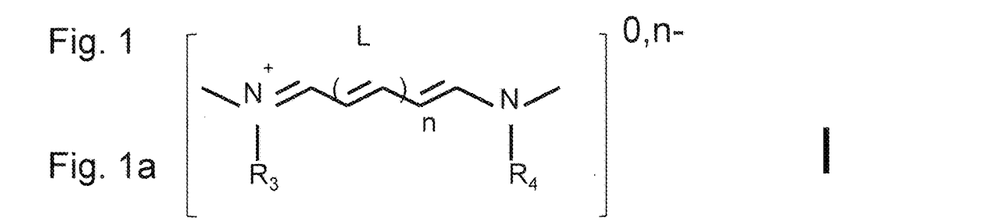
FIG. 1*a-c* shows generic structures of three main sub-families of the present cyanine. FIGS. *d* and *e* show examples of group R9 of FIGS. 1*b* and *c*.
Figure 1B:
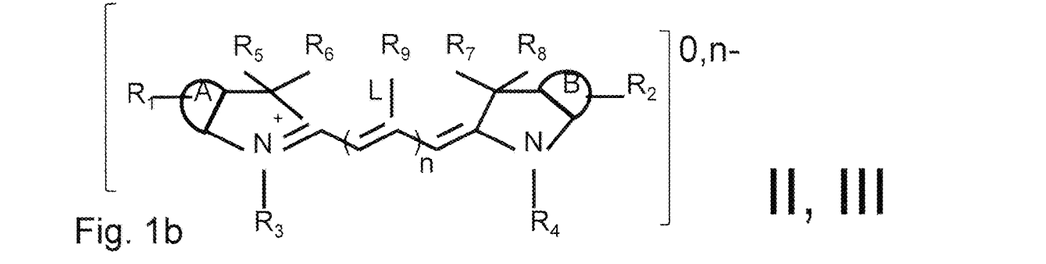
Figure 1C:
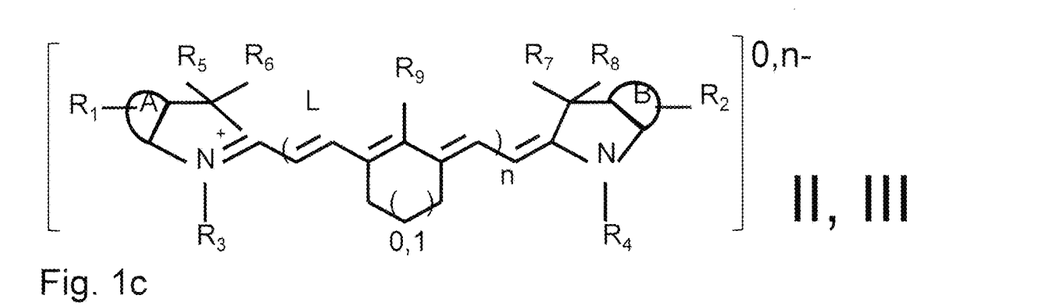
Figure 1D:
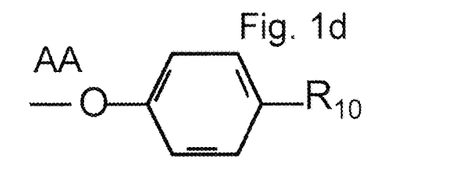
Figure 1E:
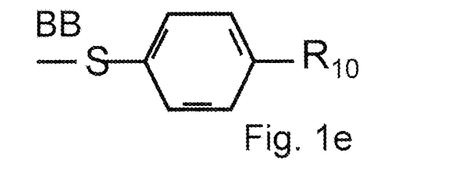
Figure 2:
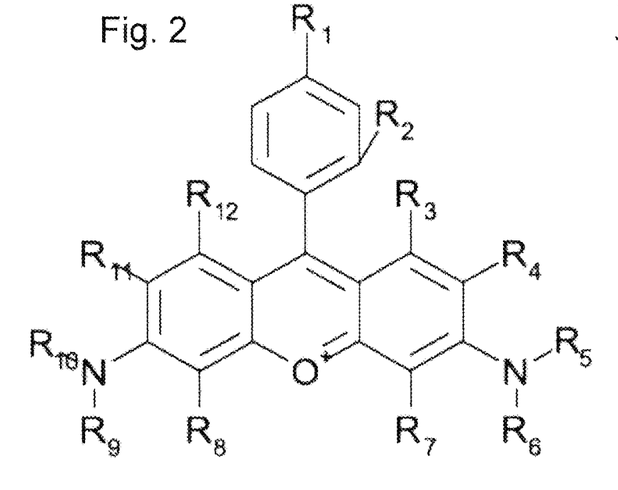
FIG. 2 shows a generic structure of a Rhodamine.
Figure 3A:
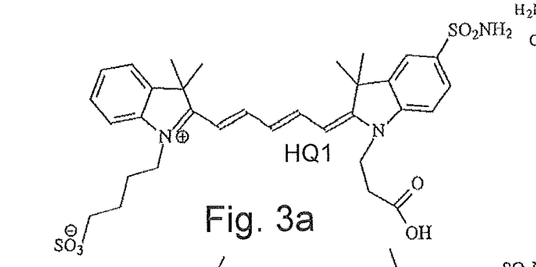
Figure 3B:
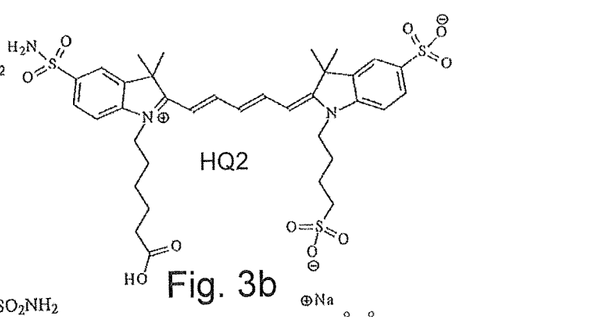
Figure 3C:
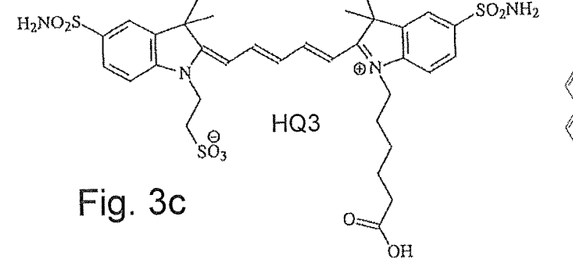
Figure 3D:
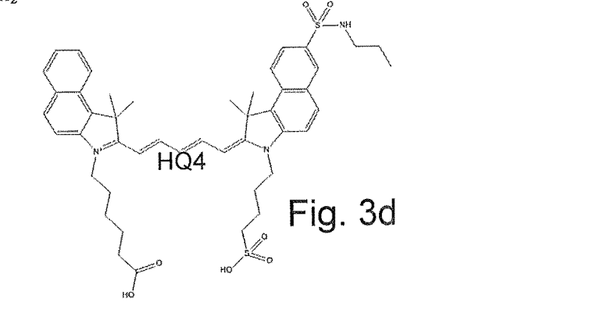
Figure 3E:
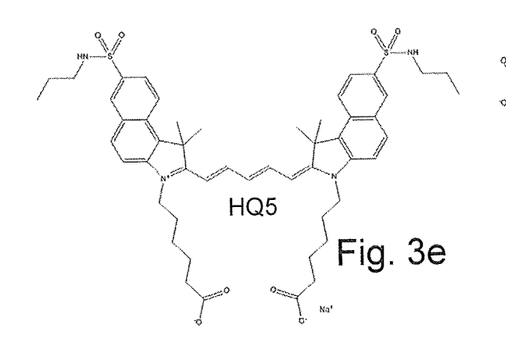
Figure 3F:
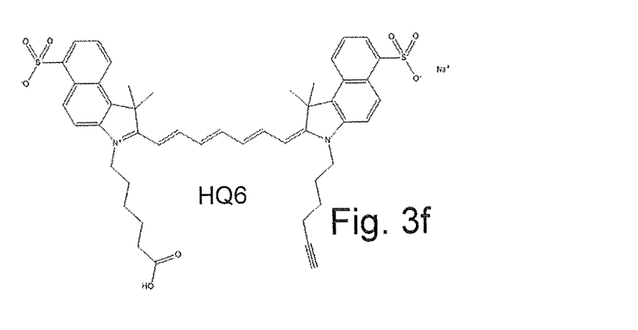
Figure 3G:
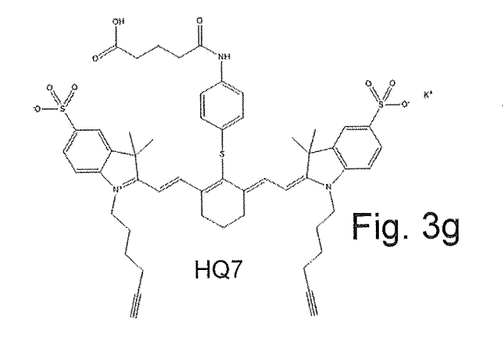
Figure 3H:
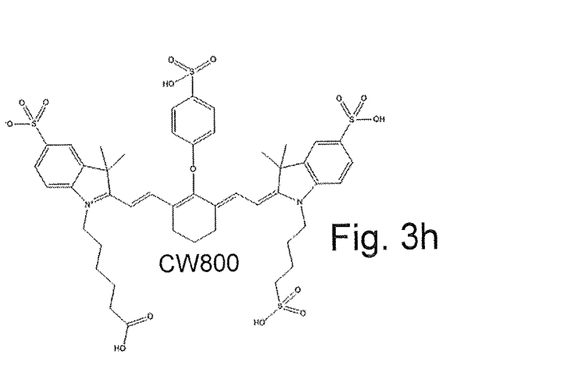
Figure 3I:
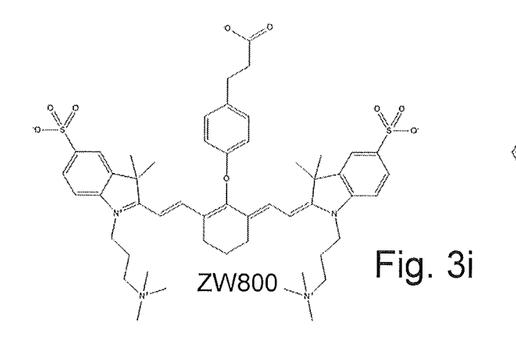
Figure 3J:
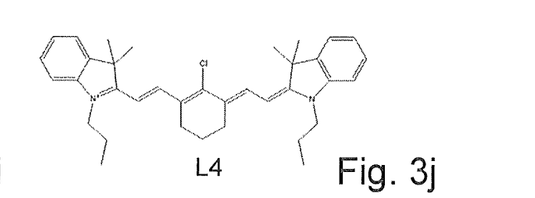
Figure 3K:
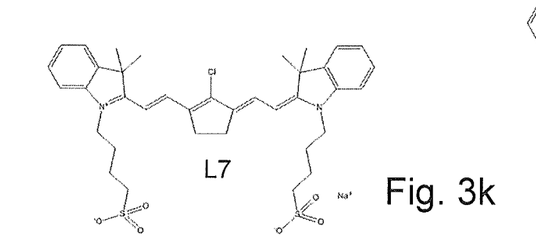
Figure 3L:
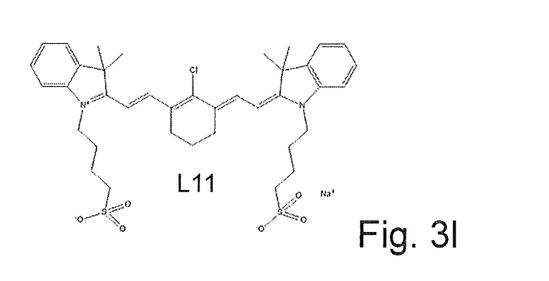
Figure 3M:
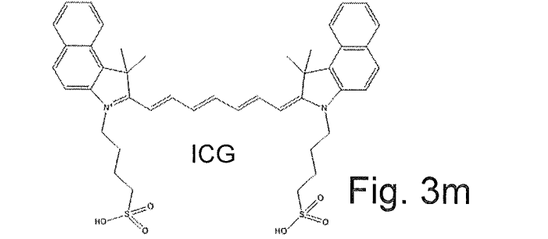
Figure 3N:
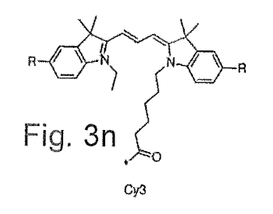
Figure 3O:
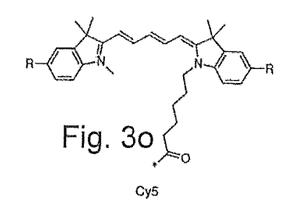
Figure 3P:
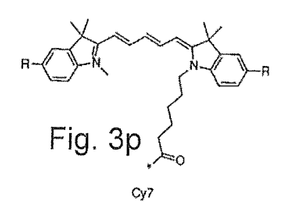
Figure 3Q:
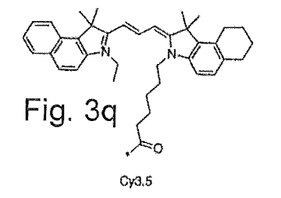
Figure 3R:
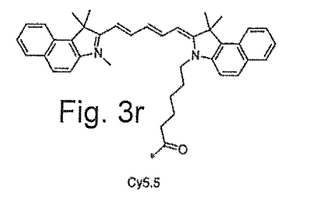
Figure 3S:
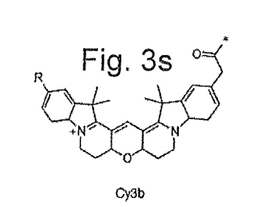
Figure 3T:
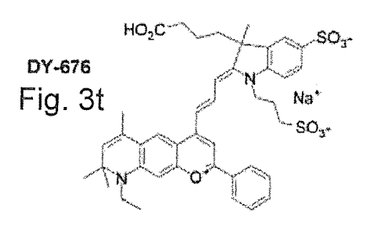
Figure 3U:
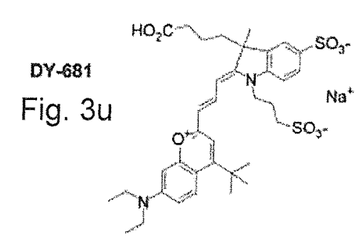
Figure 3V:
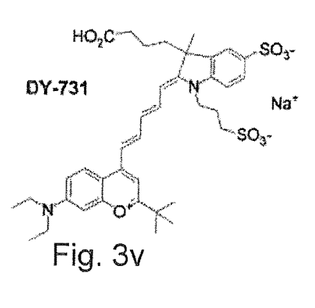
Figure 3W:
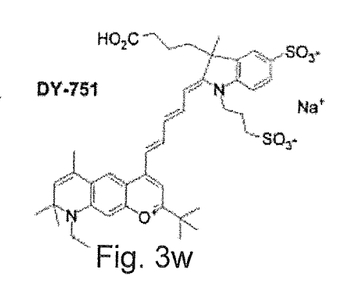
Figure 3X:
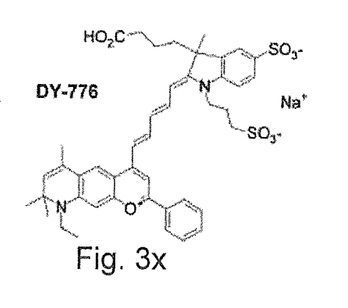

The terms cyanine and rhodamine are defined with reference to the structures of FIGS. 1 and 2 and to the associated descriptions of these Figures.

Detecting cell death includes detecting dead, dying and/or decaying cells, preferably dead cells. Cells undergoing apoptosis or necrosis are examples of dying cells; a person of skill in the art is familiar with the characteristics of a cell undergoing such a mechanism and is capable of determining such.

The general term luminescent compound and the corresponding term luminescence are used to refer to a compound that is capable of emitting light e.g. following excitation, at least under certain conditions, such as when bound to a cell constituent, such as a protein. The term "light" is taken to relate to an emission of radiation having a wavelength in the range of 200-2500 nm, preferably from 400-1500 nm. Infrared light/radiation is defined as having a wavelength within these ranges, but being greater than about 700 nm, such as greater than 850 nm. Luminescence is not limited to emission from a singlet excited state, but also to emission from multiplet excited states. Wherein the term fluorescent or fluorescence is used, this relates to compounds whose emissive state is a singlet excited state. Such terms and their meanings are familiar to a person of skill in the art.

Apoptosis and Necrosis and their meanings have been discussed with relation to the prior art.

It is a big advantage that the present compounds are capable to penetrate a cell, once a cell starts dying, and specifically when it is dead. Such as somewhat atypical, as many compounds in general, and specifically luminescent compounds such as those of the invention, typically having a molecular weight of about 500 Da or greater, often being lipophilic and/or being charged, are not capable of penetrating a cell, e.g. as these compounds are hindered by the cell membrane or bind non-specifically for example to cell membrane components. The present compounds are therefore very suitable for detecting such decay or cell death.

The present biomarker have good statistical sensitivity (e.g. ≥0.9), and good statistical specificity (e.g. ≥0.9). It is noted that if these are chosen with a population in mind positive predictive value and negative predictive value are even more relevant.

It has been found experimentally that the present compounds interact with a cell, if the cell starts dying or is dead, by having a chemical, physical and/or biological interaction, referred to as interacting chemically/physically/biologically. Such interaction may relate to a chemical bond, to a hydrogen bond, to an ion-ion interaction, to a dipole-dipole interaction, to a pi-stacking interaction and combinations thereof, or to incorporation into a dead cell or an organelle of said dead cell i.e. the present compound and a cell, or a constituent thereof, interact. It is believed the interaction takes place inside a cell.

Surprisingly the interaction takes place directly between the present compound and the cell, or constituent thereof. In prior art methods typically a vector is used to which the luminescent compound is attached. Typically the vector gives specificity for a particular cell component e.g. the vector may be a substrate for a particular enzyme, a DNA and a RNA sequence. The combination formed accordingly is than attached to a cell or cell constituent. Such is less effective, e.g. in terms of relative amount of compound/marker interacting with a cell, more costly, more toxic, etc. The cell and specifically the constituent thereof are typically not accessible (for the present compound) in living or dying cells. The (first) cell constituent may relate to a compound that is a decay product of a dead cell, such as a protein, to a compound that is present on an inside or in a cell, etc.

The present population of cells may be present in an animal or human body, or in a sample such as for use in an in vitro assay. Typically the population will comprise one or more of living cells, dying cells and decaying cells.

The present compounds are contacted with the population of cells during a predefined period of time, which period is long enough to establish substantial interaction between the compounds and the population, if cell death is occurring therein. Typically said period is in the order of seconds-hours such as of the order of 1-360 minutes, depending on the population of cells and (luminescent) compound used. Typically a very small amount of present first compound, such as 1-500 nanomole per kg cells, e.g. 2-100 nanomole per kg cells, is sufficient to obtain detectable interaction. From the amount of compound added most compound interacts with dead cell, such as a relatively fraction of more than $10^6$, typically more than $10^9$, that is only one molecules of first compound does not interact with a dead cell compared to a huge number of molecules that does interact with a dead cell.

Optionally the present compounds, and possible other constituents, chemicals, etc. being present are washed. Such improves a signal to noise ratio to be obtained.

The compounds interacting with dying or dead cells remain in the sample or body.

Subsequently emission and absorption characteristics of the compounds can be determined. Such depends e.g. on the type of compound used, the interaction, the technique used to determine the characteristics, etc. Examples of emission characteristics include luminescence intensity, luminescence lifetime, red-shift or blue-shift in the emission spectrum, change in quantum yield, change in the form of the emission spectrum.

The emission characteristic may be measured either as an average over the sample, or values of the emission characteristic may be related to sample coordinates e.g. identifying the location of dead cell(s) in a sample of cells.

Determination of cell death involves determining a change in a characteristic, such as relative to a reference state as a result of the luminescent compound interacting with dead, dying and/or decaying cells. Therewith the present invention provides a very sensitive, accurate, very localized, etc. method for determining cell death. It is noted that the present method can determine very small domains of dying cells, or dead cells, e.g. a square or cubic domain having a side length in the order of 1-100 μm, such as 5-500 μm. As such a relevant parameter can be determined in very early stage of a disease, e.g. cancer, etc., and effects or absence of treatment, e.g. with chemotherapy, can also be determined e.g. within a few hours. For instance, if chemotherapy is not effective, no or hardly any signal will be obtained, and such can be established almost immediately. The chemotherapy can than be stopped, and e.g. another therapy can be tested. As animal bodies can typically withstand only a few therapies, it is of great advantage to stop a non-effective therapy at once.

The present invention overcomes one or more of the above mentioned problems and/or disadvantages and provides further advantages, as detailed throughout the description. It is noted that the present invention also relates to combinations of two or more of the embodiments/examples provided.

DETAILED DESCRIPTION OF THE INVENTION

The present invention relates in a first aspect to a method for determining a value or values of one or more parameters of a biological sample according to claim 1.

In an example the cyanine and rhodamine containing compounds may relate to compounds with e.g. a cyanine or rhodamine core structure, as per FIGS. 1 and 2, that is comprising further (functional) groups, molecules, atoms, attached to the cyanine or rhodamine, and combinations thereof.

Non-toxic indicates that the compound does not cause significant cell death or cell deterioration in concentrations required for the method of the invention. Furthermore, in an exemplary embodiment, non-toxic indicates that the compound may be administered to a patient, e.g. intravenously, at concentrations of up to 10 mg/kg of body weight up to 2× in one day, preferably less than 1 mg per body weight.

In an exemplary embodiment a value or values of the measurement above a threshold value indicate binding of the compound to the first cell constituent. Typically the present measurement is somewhat biased by boundary conditions. Therefore a value is preferably determined above a certain threshold, e.g. 0.0001 μM. Such threshold can be determined experimentally, if necessary on a case to case basis.

In an exemplary embodiment of the method the one or more parameters is the presence and/or concentration and/or location of dead cells in the population of cells. Such is a big advantage as very low concentrations and/or very small locations comprising the dead or dying cells can be measured with high precision and accuracy.

In an exemplary embodiment of the method the suitable imaging technique is selected from a group comprising: emission spectroscopy, MRI, PET, SPECT, CT and combinations thereof. The present invention is especially suited for use in well developed technologies and improvements thereof. As such advantages of the imaging techniques, such as resolution, can be incorporated in the present method.

In an exemplary embodiment of the method the cyanine and/or rhodamine is a light emissive cyanine or rhodamine in a wavelength range of 200 nm-2500 nm, preferably an infrared wavelength. It has been found experimentally that very sensitive and accurate results are obtained when light is used as emission, in particular having a wavelength of 200 nm-2500 nm (UV-near infra-red). Especially the longer wavelengths are very well suited in this respect, e.g. having a wavelength of 600-2500 nm, preferably from 600-1500 nm.

In an exemplary embodiment of the method the first cell constituent is a protein, said protein optionally being a biomarker for cell death. Said protein is preferably selected from the group comprising fibrous proteins, such as 40 kDa proteins, 100 kDa proteins, such as tubulin, such as α-tubulin, β-tubulin, γ-tubulin, δ-tubulin and ε-tubulin, actin, such as G-actin, and F-actin, fibrous structural proteins, such as keratin, such as neutral, basic or acidic keratin, such as keratin 1-keratin 20, metalloenzymes, such as enolase, and lyase, CDC37, preferably tubulin or actin, isomers thereof, complexes thereof, and decay products thereof.

A biomarker is a compound e.g. a protein, which is objectively measured and evaluated as an indicator of normal biologic processes, pathogenic processes, or pharmacologic responses to a therapeutic intervention. In the present context, a biomarker for cell death is a protein whose presence in the environment of the rhodamine or cyanine is indicative of cell death. In the environment is taken to mean such that they can come into contact.

It is noted that typically a huge amount of proteins and in a large variety is present in a cell. Presence of many of these proteins, as well as DNA, RNA, etc. does not correlate with dead or dying cells.

In an exemplary embodiment of the method the cyanine and/or rhodamine is a non-activated or deactivated compound, therewith substantially preventing other interaction, such as with amines, such as one of HQ4, HQ5, HQ6, HQ7, ICG, CW 800, ZW800, L4, L7, L11, CY3, CY3b, CY3.5, CY5, CY5.5, CY7, DY-676, DY-681, DY-731, DY-751, and DY-776, and conjugable derivatives thereof. These compounds have been found to be very effective, e.g. in terms of specificity, detectability, etc. The term conjugable derivative means that the compound comprises the structure of one of the above compounds and a further functional group such as an acid or amine group allowing conjugation to another molecule. The term conjugable is considered to be known to a person of skill in the art in this context.

Said compounds have been found to bind specifically to dying cells and/or their constituents, such as through binding to a protein therein; detecting cell death is already possible during the first stadium (leaking of the membrane); they connect to a specific protein and not to bloodcells or DNA, and; these compounds have very favorable photophysical properties allowing them to be used in a low dose e.g. high quantum yield, low susceptibility to quenching.

The group of present compounds has been tested experimentally, It has been found that especially the compounds of FIG. 1 are very well suited, e.g. in terms of specificity, accuracy, localization, etc.

In an exemplary embodiment of the method the cyanine and/or rhodamine is coupled to one or more of: (i) a radio-active tracer; (ii) an MRI contrast agent; (iii) a microbubble for ultrasound or opto-acoustic imaging; (iv) a nanoparticle; (v) a molecule suitable for imaging, and (vi) a biological active compound. As such the present invention provides a wide variety of application, e.g. in determining characteristics thereof, in terms of optional further compounds being bonded thereto. The present compound functions in this respect also as a vector. It has been found experimentally that certain combinations of the present first compounds (two or more) have superior interaction characteristics.

In an example a radio-active tracer may be used, coupled to the present biomarker, e.g. suitable for PET or SPECT.

In an example an MRI-contrast agent is coupled, suitable for use in an MRI-apparatus.

In an example a microbubble is coupled, suitable for use with e.g. ultrasound or opto-acoustic imaging. Even further a coupled compound or microbubble or particle may be activated accordingly.

In an example a nanoparticle is attached, e.g. for transporting an active agent.

The tracer, MRI-contrast agent, microbubble, nanoparticle, etc. can subsequently be localized with high specificity, accuracy, localization, etc.

Examples of the above relate to linking of a chelating moiety (e.g. DOTA-like moieties) that can bind an isotope or the like, such as $^{111}In^{3+}$, making the method suitable for SPECT. Likewise an isotope, such as $^{18}F$, may be used, making the method suitable for PET. Likewise and isotope as $^{19}F$, may be used, making the method suitable for MRI.

In an exemplary embodiment the population of cells is in a sample, and step (i) of claim 1 comprises one or more of: (i) measuring luminescence intensity of the compound(s) on the sample as an average over the sample, and; (ii) measuring luminescence intensities of the compound(s) on the sample such that they relate to sample coordinates.

As mentioned above the present method provides a very precise determination of coordinates, or localization, of luminescence. Even further, the intensity of the luminescence provides information on an amount of dying or dead cells being present within said locality. Also luminescence could be measured as an average over a sample, thereby providing an impression of an amount of dying and/or dead cells within the sample. Both the averaged and localized intensities provide useful information, e.g. on the status of cells.

In an exemplary embodiment of the method, detecting cell death comprises comparing the measured emission characteristics of the compound(s) on the population of cells with a set of reference values. Typically a calibration curve, reference values, or the like will be established. Measured characteristics will then subsequently be compared to said reference values, in order to determine actual amounts for the population of cells.

In an exemplary embodiment of the method the interacting takes place in a time in a range of 1-360 minutes; more preferably 15-240, most preferably 120-180. In general it takes some time for the first compound to have interaction with the first cell constituent, e.g. because the two need to come into close proximity. Depending on boundary conditions, the above time is more than 1 minute. For some compounds a clear signal (value) is obtainable after approximately 15-30 minutes. The signal may even improve over time, sometimes being "optimal" after a few hours, e.g. 2-3 hours. Such implies that a patient being e.g. in a hospital and being treated, e.g. for cancer, can await first results of said treatment in the hospital. Depending on the first results further actions can be taken, if necessary, treatment can be stopped or continued, etc.

The present invention relates in a second aspect to a use of the present method in an assay for screening drugs for therapy such as cancer therapy. As the present compounds can be used as targeting cells, also drugs can be coupled to the present compounds. Therewith drugs can be screened for use in therapy. The present method(s) and present use(s) may be performed in vivo, in vitro, in a dead organism, or any other way.

In an exemplary embodiment the use is to monitor and/or determine the effectiveness of a therapy. As indicated above the present method provides a real-time and accurate measure of effectiveness of therapy. Therefore such can be monitored as well, e.g. a patient entering a hospital or the like, can be administered a drug or therapy, and results thereof, or at least initial results, or absence thereof, can be monitored in a very limited time frame. The patient can remain in the hospital and await results. Subsequent steps can be taken then, if required.

The present invention relates in a third aspect to one or more of a cyanine, a rhodamine, and any other first compound according to claim 12. These compounds, and specific examples thereof, haven been described above, as well as advantages thereof.

In an exemplary embodiment the cyanine or rhodamine is one or more of: (i) negatively charged; (ii) infrared emissive; (iii) capable of binding to a protein, optionally wherein the protein is a biomarker for cell death; (iv) one of HQ4, HQ5, HQ6, HQ7, ICG, CW 800, ZW800, L4, L7, L11, CY3, CY3b, CY3.5, CY5, CY5.5, CY7, DY-676, DY-681, DY-731, DY-751, and DY-776, and a conjugable derivative thereof.

Advantages of the use of the present compounds are elucidated throughout the description.

The present invention relates in a fourth aspect to an assay kit comprising a fluid, such as a physiological fluid, a cyanine and/or rhodamine, a means for storing, and preferably consevations agents, such as an antibacterial agent, such as an azide, preferably in an amount of 0.1-5 ml and preferably in a concentration of cyanine and/or rhodamine of 0.2-50 µM. In an example a concentration of 2-20 µM and an amount of 1-2 ml are provided. Typically a user may take a sample of the assay kit, such as 10 µl thereof and dilute the sample, such as by a factor 100. Therewith a solution is obtained having a concentration of 2-500 nM of cyanine/rhodamine. As such a product is provided for e.g. use in the present method.

The present invention relates in a fifth aspect to the present compound for use in one or more of determining presence or absence of Alzheimer's disease, determining effectiveness of chemotherapy, determining cell damage in a tissue, such in a heart after a heart-attack, such as in the brains after a stroke, and cell death in a tissue. For instance, the present compound is capable of detecting any disease in which cell death is involved. The present compounds are extremely useful in determining cell death, and thus in determining associated diseases. Even further, presence or absence of Alzheimer's disease can be determined in a very early stage.

In an exemplary embodiment, cyanine and/or rhodamine is one of HQ4, HQ5, HQ6, HQ7, ICG, CW 800, ZW800, L4, L7, L11, CY3, CY3b, CY3.5, CY5, CY5.5, CY7, DY-676, DY-681, DY-731, DY-751, and DY-776, and a conjugable derivative thereof.

SUMMARY OF FIGURES

FIG. 3 *a-x* gives the structures of compounds referred to throughout the application.

FIGURES

FIG. 1a-c shows generic structures of three main sub-families of the present cyanine. Cyanine is a non-systematic name of a synthetic dye family belonging to polymethine group. Referring to the central carbon chain in FIG. 1; n is an integer, such as n∈[2,10], preferably n∈[4,8]. The n carbon atoms may have up to n−1 double bonds, and typically n/2 double bonds. Sub-families II and III comprise respectively one and two aromatic ring systems (A,B) signified by the curved line(s) C. A,B are preferably selected each individually from benzene and naphthalene. Further groups $R_5$, $R_6$, $R_7$, and $R_8$, may be present. $R_5$, $R_6$, $R_7$, and $R_8$, are preferably selected each individually from H, and alkyl, such as methyl, ethyl, and propyl, preferably methyl. Present group III is preferred, e.g. in view of functionality and present advantages. The aromatic ring systems may comprise further functional groups $R_1$, $R_2$, and/or substituents as is evident from the specific examples of FIGS. 3a-i. $R_1$, $R_2$, are preferably selected each individually from H, sulfonate, and sulfonamide. The chain of alternating single and double bonds L may be interrupted by introducing one or more partly and fully saturated ring structures, such as cyclopentane and cylcohexane, and combinations thereof, such as one or more cyclohexene rings, as is evident from FIG. 3g, the conjugation i.e. system of double and single bonds, being maintained. The saturated ring structure may further comprise functional groups groups $R_9$, $R_9$ being selected from H, AA and BB (FIGS. 1 d-e), wherein $R_{10}$ is selected from, H, $SO_3H$, Cl, —N—C=O—$(CH2)_q$—$Y_3$ (q=1-6), —$(CH2)_r$—$Y_4$ (r=1-6), $Y_3$ and $Y_4$ are each independently one of H, COOH, $SO_3H$, CN. Typically one of each nitrogen atom being present at ends of chain L (having optionally one or more further carbon atoms between the chain L and the nitrogen) is charged positively, the other being neutral. It is noted the charge may shift from one nitrogen to the other, and back. The nitrogen atoms (N) may comprise further functional N-side groups $R_3$, $R_4$, $R_3$, $R_4$ are preferably selected each individually from —$(CH_2)_m$Y. Typically such N-side groups comprise m carbon atoms, such as m∈[1,10], preferably m∈[2,8], more preferably m∈[3,7], most preferably m=4,5, and 6. Even more preferably at least one of m=4, 5, and 6, preferably one m=6 and the other m preferably is 4, 5 or 6. Preferably the side groups comprise one or more functional groups Y on an end opposing the N, such as a carboxylic acid having 1-4 carbon atoms, an sulfonate group, CN, C≡C, and C=C, and salts thereof, such as sodium and potassium salts. Most preferably the functional group on the end comprises one or more double C—C bonds.

The term cyanine refers to any compound whose core-structure is that of sub-family I, II or III. The integer in names of cyanines such as Cy 3, Cy 5, Cy 7 etc. refers to the number of carbon atoms in the chain L. In an exemplary embodiment, the cyanine belongs to one of these families.

FIG. 2 shows a generic structure of a Rhodamine; R1 to R12 can be hydrogen or a functional group, examples of suitable functional groups include sulfonic acid groups, carboxylic acid groups, sulfonamides, alcohols, amines, esters, ethers, thiols, thio esters and combinations thereof. The term Rhodamine refers to any compound whose core-structure is that shown in FIG. 2.

FIG. 3 a-x gives the structures of compounds referred to throughout the application.

FIG. 4 shows a dry-ice dead-cells-assay. Confluent cultures of 4T1-luc2 cells treated with a focal application of dry-ice to the bottom center of a culture well, subsequently incubated with Trypan Blue for 15 min, washed and scanned (A), or incubated with luciferase and imaged for bioluminescence (B).

Figure 5A:
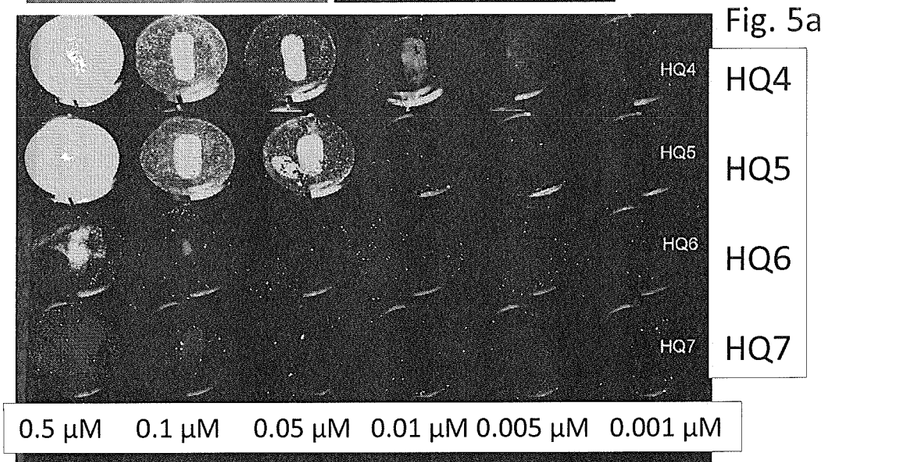
FIGS. 5A and B show a Dry-ice dead-cells-assay.
Figure 5B:
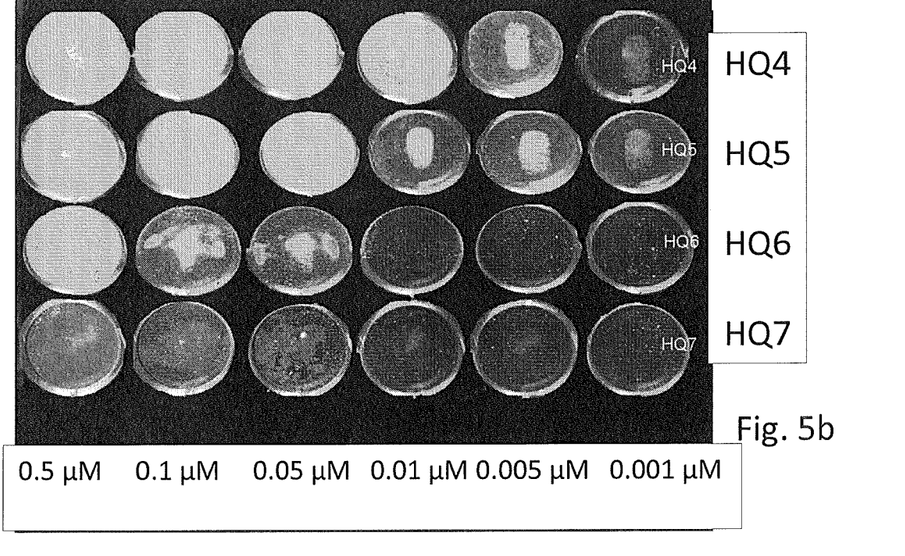

FIGS. 5A and B show a Dry-ice dead-cells-assay. Confluent cultures of 4T1-luc2 cells treated with a focal application of dry-ice to the bottom center of a culture well, subsequently incubated with HQ medical #1-7 (0.5 to 0.001 uM), washed and scanned with the Licor Odyssey. Low (A) and high (B) contrast pictures are shown.

EXAMPLES

The examples and accompanying figures are exemplary and explanatory of nature and are not limiting the scope of the invention. To the person skilled in the art it may be clear that many variants, being obvious or not, may be conceivable falling within the scope of protection, defined by the present claims.

The dead cell targeting properties of seven HQ medical compounds (HQ1-7) were assessed in a newly developed in vitro assay of living and dead 4T1-luc2 mouse breast cancer cells. For this 4T1-luc2 cells were cultured to confluence in 12-well plates and a local area of cell death was induced by applying a bar of dry ice to the bottom of the culture well. Subsequently, the cells were incubated with the test compounds, washed and imaged with the Lycor Odyssey.

In summary, inventors found that HQ medical compounds #4, 5, 6 and 7 all showed excellent specificity towards dead cells. Also ICG, CW 800, ZW800, L4, L7, L11, CY3, CY3b, CY3.5, CY5, CY5.5, CY7, DY-676, DY-681, DY-731, DY-751, and DY-776 all showed specific binding to dead cells. Of these four compounds, both HQ medical #4 and 5 were the most potent dead cell detectors and even after incubation with a concentration as low as 0.001 μMa specific signal was detectible. For HQ medical #6 and 7, a signal from the dead cell area could be detected at least 50-fold higher concentrations. Therefore we conclude that, at least in our in vitro assay, HQ #4 and HQ #5 are highly specific and sensitive detectors of dead cells.

Materials and Methods

Compound Tested:

| HQ | Molecular weight | Emission (nm) | Absorbance (nm) |
|---|---|---|---|
| #1: | 641.80 | 664 | 642 |
| #2 | 785.92 | 668 | 649 |
| #3 | 734.90 | 666 | 647 |
| #4 | 826.08 | 701 | 682 |
| #5 | 947.19 | 701 | 683 |
| #6 | 830.98 | 694 | 675 |
| #7 | 1061.34 | 816 | 797 |

In Vitro Model of Cryo-Induced Cell Death

4T1-Luc cells were seeded onto individual wells from a 12-well cell culture plate and allowed to grow to confluence in RPMI media supplemented with 10% fetal bovine serum. 4T1-luc2 mouse breast cancer cells were used as the adherence of these cells to the bottom of the culture well remains strong after dry-ice treatment. To initiate cryo-induced cell death, media was discarded and dry-ice was applied to the bottom center of each individual well for 15 sec. Subsequently, fresh medium with different concentrations of the HQ medical compounds (HQ1-7) were added and cells were incubated at 37° C. for 15 min. After incubation, the media were discarded and the cells were washed twice with serum free medium and 0.5 ml fresh RPMI was added to each well. Cells were then visualized using a Licor Odyssey equipped with 700 and 800 nm diode laser. Luciferin (1.25 mg/kg) was also added to each well and fluorescence and biolumi- nescence images were acquired using an IVIS Spectrum (fluorescence: excitation filter: 710 nm, emission filter: 820 nm, exposure time: 90 s, bin: 8, f/stop: 2, field of view: 12.9 cm) (bioluminescence: open filter, exposure time: 30 s, bin: 8, f/stop: 1, field of view: 12.9 cm). Some culture wells were also stained for 15 min with Trypan Blue (0.2% in culture medium) to confirm cell death.

Results and Discussion

In Vitro Imaging of Dead Cells

Dry-Ice Dead-Cells-Assay

Figures 4A, 4B:
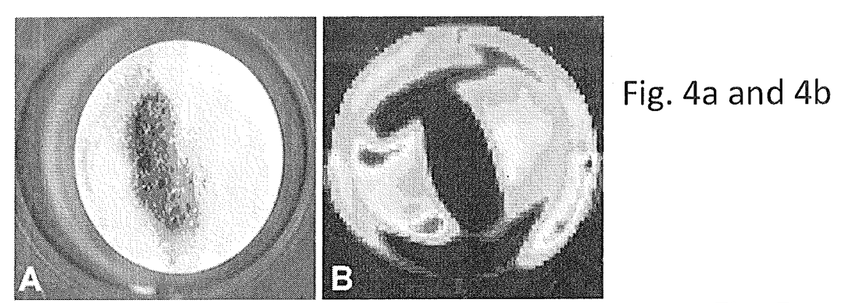
FIG. 4 shows a dry-ice dead-cells-assay.

Confluent cultures of 4T1-luc2 breast cancer cells were treated for 15 sec with a focal application of dry-ice to the bottom center of a culture well and were used to examine the dead cell binding properties of the seven HQ medical NIRF compounds. First, however, in order to confirm the presence of a local area of dead cells, the dry-ice treated cultures were incubated with Trypan blue or were treated with luciferin and measured for bioluminescence. As shown in FIG. 4A, the cells at the site of focal dry-ice treatment showed an increased uptake of Trypan Blue as compared to the viable cells in the periphery. This indicates that cells in the center are dead and those in the periphery are viable. In line, as indicated by BLI measurement, the cells in the periphery showed a strong bioluminescence signal whereas no signal was obtained from the cells in the area of dry-ice treatment (FIG. 4B).

HQ Medical NIRF Compounds for Imaging Dead Cells In Vitro

HQ medical #1-7 were examined for their imaging potential of dead cells in the present dry-ice dead-cells-assay. The cells were incubated with the HQ medical compounds with concentrations ranging from 0.5 to 0.001 uM. HQ medical #4-7, all specifically bound to dead cells (FIGS. 5A and B). From these four compounds, both HQ medical #4 and 5 were the most potent dead cell detectors and even after incubation with a concentration as low as 1.0 nM a specific signal from the cells was detectible. For HQ medical #6 and 7, a signal from the dead cell area could be detected at least 50-fold higher concentrations.

It is noted that compounds such as Annexin-V do not bind to proteins inside a cell, typically not within a nucleus thereof.

The invention claimed is:

1. A method for providing an image of one or more parameters of a biological sample, said biological sample comprising a population of cells in a tissue comprising naturally occurring dead necrotic cells and living cells, the method comprising the steps of:
   providing the biological sample;
   contacting the biological sample with at least a first compound,
   said dead cells having at least a first cell constituent substantially present and/or accessible to the at least first compound only in dead cells, wherein the first compound is selected from a group consisting of negatively charged non-toxic cyanine containing compounds and wherein the cyanine containing compound is a non-activated or deactivated compound, and wherein the cyanine in the first compound is targeting said first cell constituent by selectively interacting chemically/physically/biologically directly with the at least the first cell constituent thereby forming a complex, wherein the first cell constituent is at least one intracellular cell protein, wherein said intracellular protein is selected from the group comprising fibrous proteins, fibrous structural proteins, metalloenzymes, isomers thereof, complexes thereof, and decay products thereof;
   performing one or more measurements on the biological sample and first compound with at least a first suitable imaging technique providing the image, wherein the suitable imaging technique is selected from a group comprising:
   emission spectroscopy, Magnetic Resonance Imaging (MRI), Positron Emission Tomography (PET), Single Photon Emission Computed Tomography (SPECT), Computed Tomography (CT), optical imaging, microscopy, acoustical imaging, and combinations thereof, wherein the measurement indicates binding of the compound to the first cell constituent, and;
   analysing said measurement to determine the one or more parameters,
   wherein the one or more parameters is the presence and/or concentration and/or location of dead cells in the population of cells,
   optionally by comparison with a set of references;
   wherein the cyanine is a non-activated or de-activated cyanine, according to FIG. 1 I, II and III, wherein sub-families II and III comprise respectively one and two aromatic ring systems (A,B) signified by the curved line(s) and A,B are selected each individually from benzene and naphthalene, R1, R2, are selected each individually from H, sulfonate, and sulfonamide, R3, R4 are selected each individually from (CH2)mY, wherein Y is selected each individually from a carboxylic acid having 1-4 carbon atoms, a sulfonate group, CN, C≡C, and C=C, and salts thereof, R5, R6, R7, and R8, are selected each individually from H, and alkyl, and R9 being selected from H, AA and BB, n is an integer wherein nÎ[2,10], and the chain L has up to n−1 double bonds.

2. The method according to claim 1, wherein the cyanine is a light emissive cyanine in a wavelength range of 200 nm-2500 nm.

3. The method according to claim 1, wherein the cyanine is coupled to one or more of: (i) a radio-active tracer; (ii) an MRI contrast agent; (iii) a microbubble for ultrasound or opto-acoustic imaging; (iv) a nanoparticle; (v) a molecule suitable for imaging, and (vi) a biological active compound.

4. The method according to claim 1, wherein the interacting takes place in a time in a range of 1-360 minutes.

5. The method of claim 1, further comprising using the method in an assay for screening drugs for therapy.

6. The method of claim 1, further comprising using the method to monitor and/or determine the effectiveness of a therapy.

7. The method according to claim 1, wherein said protein is selected from the group consisting of α-tubulin, β-tubulin, γ-tubulin, δ-tubulin and ε-tubulin, G-actin, F-actin, keratin 1 keratin 20, enolase, lyase, isomers thereof, complexes thereof, and decay products thereof.

8. The method according to claim 4, wherein the interacting takes place in a time in a range of 120-180 minutes.

9. The method according to claim 1, wherein the intracellular protein has a molecular weight of 40±4 kiloDaltons.

* * * * *